United States Patent [19]

Hofmeister et al.

[11] Patent Number: 4,757,823

[45] Date of Patent: Jul. 19, 1988

[54] METHOD AND APPARATUS FOR MEASURING UTERINE BLOOD FLOW

[76] Inventors: John F. Hofmeister, 3860 E. Easter Pl., Littleton, Colo. 80122; Donald G. Ellis, Geneva Park, Boulder, Colo. 80302-7162

[21] Appl. No.: 6,777

[22] Filed: Jan. 27, 1987

[51] Int. Cl.$^4$ .............................................. A61B 10/00
[52] U.S. Cl. ................................ 128/663; 74/471 XY
[58] Field of Search ................................. 128/660-663, 128/305, 738, 643, 778; 74/471 R, 471 XY

[56] References Cited

U.S. PATENT DOCUMENTS

| | | | |
|---|---|---|---|
| 3,893,449 | 7/1975 | Lee et al. | 128/661 |
| 4,271,706 | 6/1981 | Ledley | 128/660 X |
| 4,355,643 | 10/1982 | Laughlin et al. | 128/663 |
| 4,545,386 | 10/1985 | Hetry et al. | 128/660 |
| 4,577,640 | 3/1986 | Hofmeister | 128/738 |

OTHER PUBLICATIONS

Doriot, P. A. et al, "Quantitative Analysis of Flow Conditions in Simulated Vessels and Large Human Arteries and Veins by Means of Ultrasound", Conf.: Proceedings of 2nd European Congress on UTS in Medicine, Munich, Germany, May 12-16, 1975, pp. 160-168.

Primary Examiner—Francis J. Jaworski
Attorney, Agent, or Firm—Edwin L. Spangler, Jr.

[57] ABSTRACT

This invention relates to a method for measuring uterine artery blood flow characterized by non-invasively positioning a transducer crystal capable of generating an ultrasonic signal within the vagina of a human female at the lateral aspect of the cervix underneath and in close proximity to the uterine artery, measuring the internal diameter of the artery by sweeping the transducer thereacross through an arc lying in a plane substantially perpendicular to the flow of blood therethrough for the purpose of determining its cross section, redirecting the transducer along the artery at an acute angle opposing the direction of blood flow therethrough while impinging upon the latter a pulsed series of ultrasonic signals of known frequency, detecting the reflections of the pulsed signals and measuring the shift in the frequency of the reflections for the purpose of determining a mean velocity of the blood flowing through the artery by applying the Doppler Effect principle, and determining the blood flow volume based upon the aforesaid velocity and cross-sectional area measurements. The invention also encompasses the novel apparatus for measuring the internal diameter of the uterine artery and the velocity of the blood flowing therethrough which includes a cervical cup sized to fit the subject's cervix and define a stable platform for supporting the transducer in substantially fixed position underneath the artery, a transducer carrier mounted outside of the cup for movement relative thereto about at least one axis of rotational movement, and a remote actuator subassembly for shifting the position of the transducer located externally of the subject's body and operatively connected to the carrier through the vagina.

13 Claims, 4 Drawing Sheets

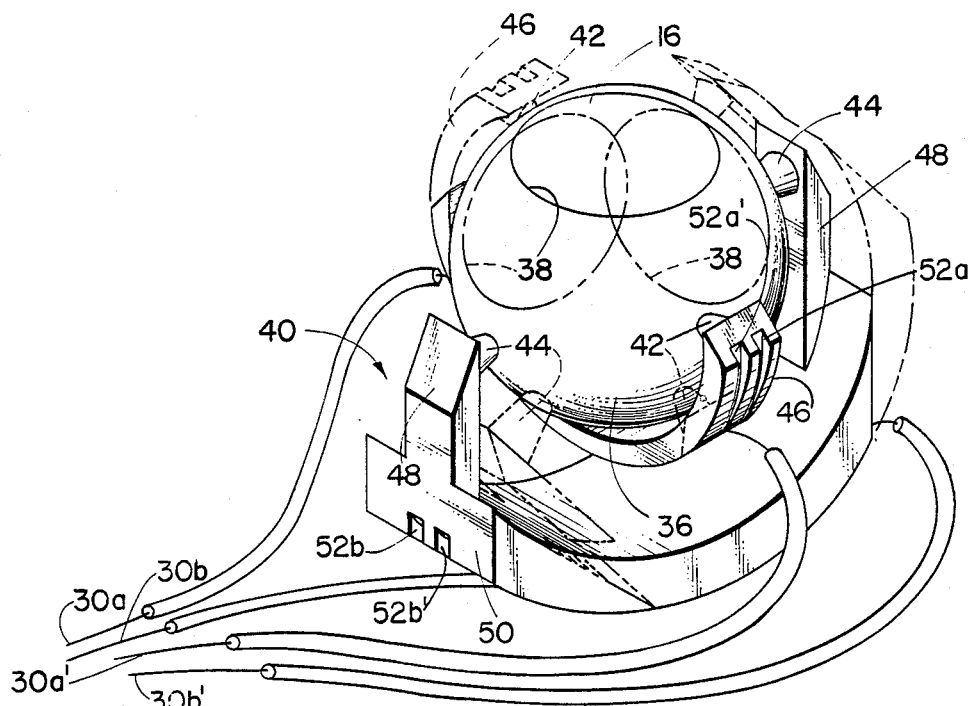
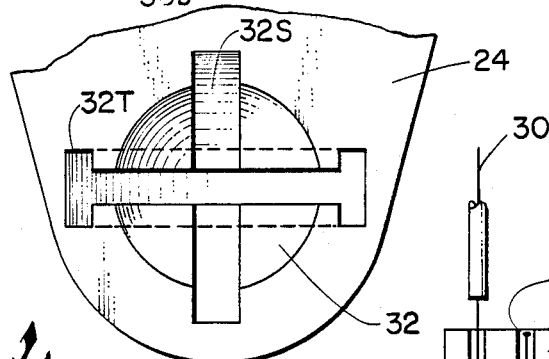
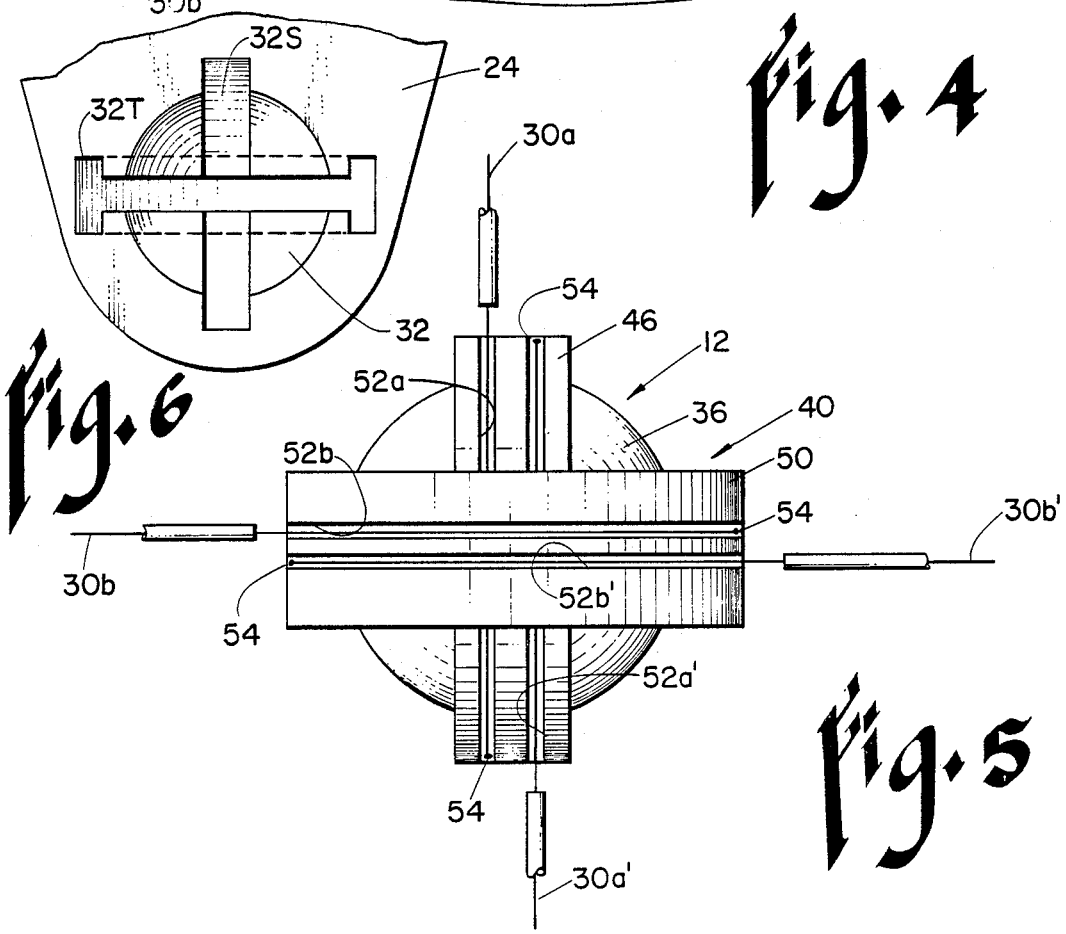

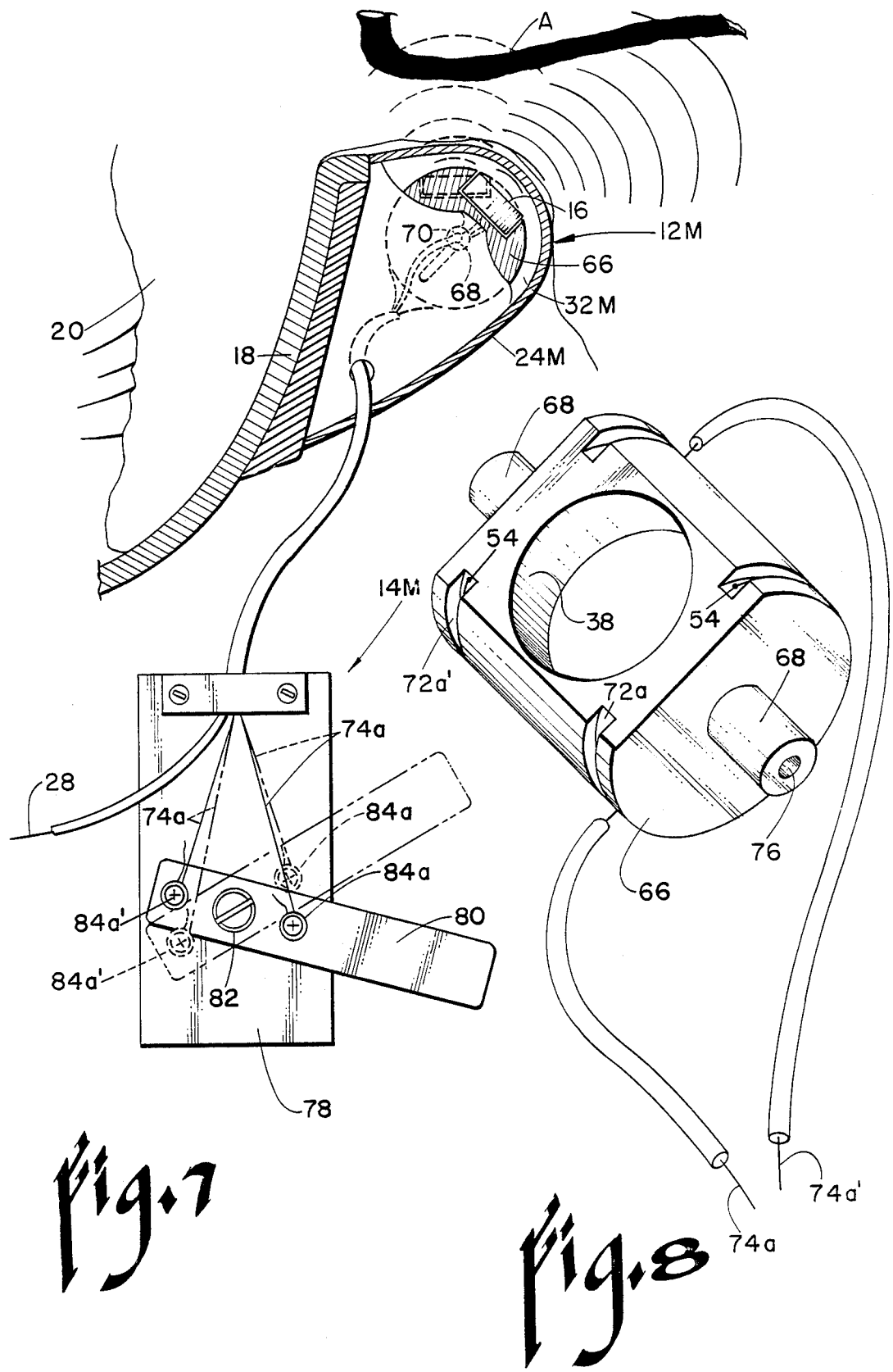

METHOD AND APPARATUS FOR MEASURING UTERINE BLOOD FLOW

BACKGROUND OF THE INVENTION

It is, of course, well known that blood flows to the uterus through a network of arteries and drains through a network of veins. The heart pumps blood through the arteries under considerable pressure (80-180 mm Hg) and these vessels have a thick muscular wall to withstand these forces. The veins are a low pressure system (approximately 13 mm Hg) and the walls of these vessels are comparatively quite thin. Almost all blood flow problems of the uterus are now thought to involve the high pressure arterial system, not the venous system.

Adequate uterine blood flow is so critical to the organism that its arteries are organized in a special highly protective configuration reserved for the certain vital organs, e.g. the brain. It is this protective arrangement that is responsible to a considerable degree for the difficulties associated with measuring uterine blood flow. Specifically, the configuration employed to protect the body's vital organs comprises an arterial loop which is fed by two arteries.

In the case of the uterus, its principal blood supply comes from the left and right uterine arteries which arise from large arteries in the left and right lateral pelvis and curve across the pelvis to meet the uterus at mid cervix. At the cervix each uterine artery bends upward and runs along the lateral aspect of the body of the uterus. Smaller arteries (arterioles) branch from this vessel and extend into the body of the uterus. By the best current estimates, the left and right uterine arteries supply about 80-90% of the blood supply of the uterus. A protective loop is formed by the small ovarian artery which arises from the aorta and joins the uterine artery near the top of the uterus. This dual arterial supply can provide enough blood to keep the uterine tissue alive if a uterine artery becomes blocked.

A very useful diagnostic tool arises from the fact that blood flow in the uterine and ovarian arteries varies with pressure and, therefore, is phasic in nature. Actually, the pattern is a bi-phasic one in that as the heart contracts and forces a bolus of blood out into the arteries, there is a sharp increase in flow in the uterine arteries. Conversely, during the cardiac relaxation phase, uterine artery flow shows a variable pattern of decline. The flow patterns of the high velocity (systolic) phase and the low velocity (diastolic) phase provide a great deal of information about the physiologic state of the uterus, and, more importantly, a fetus, which would be of considerable value if, in fact, it could be measured.

Accordingly, researchers and physicians have long sought a non-invasive method to measure blood flow in the uterine arteries of human subjects. Normal function of the reproductive system in a human depends upon adequate blood flow to the reproductive organs. It is critical to growth and to the normal physiologic activity of the pregnant and non-pregnant uterus. Impaired blood flow during pregnancy is associated with retardation of fetal development and brain damage, a major cause of perinatal mortality and permanent neurologic disability. Abnormalities of blood flow may also be implicated in several pathologic conditions associated with the uterus such as, for example, dysmenorrhea, chronic pelvic pain syndromes, and possibly endometriosis and other conditions of the non-pregnant state. The dynamics of uterine blood flow in humans are not well understood because a practical method of measuring uterine blood flow has yet to be achieved. As a consequence, most diagnoses of abnormal uterine artery blood flow are presumptive, i.e. inferred from pathologic findings consistent with impairment of the blood supply.

FIELD OF THE INVENTION

The present invention relates, therefore, to a method and apparatus for measuring uterine blood flow non-invasively and without traumatizing the area under study, all through the use of an externally-manipulated transducer.

DESCRIPTION OF THE RELATED ART

Since about the year 1967, light emitting diodes and detectors have been used for non-invasive measurements of blood flow patterns in the superficial capillary vessels of the cervix and uterus (see Hon U.S. Pat. No. 4,541,439). This method is limited to measurements of blood flow patterns and cannot as yet be used to measure the volume of blood flow in these vessels. The method is not used, and in all probability could not, be used for measurements of blood flow or volume in larger vessels (e.g. uterine arteries) because the penetration of light waves in tissue is limited to a few millimeters, whereas, penetration of at least of 3-5 centimeters is required to reach the uterine artery and measure its blood flow.

Blood flow in the uterine artery has, however, been successfully measured in animals with an electromagnetic flowmeter Gulvog et al, 1980 (Acta Phsiol Scand 109, 211-216) and Westersten's U.S. Pat. No. 3,712,133), but this not suitable for humans because major abdominal surgery is required to expose the artery for placement of the transducer. Also, radioisotopes and steady state diffusion methods have been used with animals for years, but their use entails far too many risks and adverse consequences for human subjects (Makowski 1977).

Ultrasound is, of course, a diagnostic method employed by the medical profession and associated disciplines to visualize and measure internal body structures and the movement of these structures and fluids. Within the last several decades, Doppler ultrasound has become the accepted method of measuring blood flow in cardiovascular medicine. It is an ideal non-invasive method for measuring both blood flow patterns and flow volume in human subjects. Since sound waves penetrate tissues more efficiently than light waves (millimeters vs. centimeters), this method can visualize or measure much deeper structures. Ultrasound poses little if any risk to the subject and, for this and other reasons, is now widely used in clinical medicine; however, its applicability to the uterine arteries has met with only limited success because of persistent technical problems. To begin with, the uterine arteries are located deep in the pelvis and they are surrounded by large bone and muscle masses along with an air-filled bowel, all of which serve to scatter and/or absorb the ultrasound signals. As a consequence, resolution with externally-placed transducers has been poor because of attenuation of the signals and the need to use a sub-optimum angle of sonication to avoid these large bone and muscle masses, i.e. 60° instead of an optimum 5° to 20°.

In the specific application of the ultrasound technique, high frequency sound waves well above the audible range (1.5-10 million cycles/second) are transmitted into the body and the measurements are derived from waves reflected back from body structures and fluids. The waves are generated by exciting a small crystal with electrical pulses. Evidence to date indicates that if the average power supplied to the crystal is held below approximately 100 milliwatts/cm$^2$, the ultrasound waves are not harmful to adult subjects or even a fetus. While ultrasound waves can be generated either continuously (so-called "c w" or continuous wave ultrasound) or in brief pulses (pulsed ultrasound) the preferred method employed in accordance with the teaching of the present invention to measure uterine blood flow utilizes the pulsed technique because it can provide spacial resolution, however, continuous wave ultrasound should, by no means, be ruled out. Actually, to achieve a measurement of the flow, it is necessary to measure two parameters from which flow can be calculated. Specifically, it is necessary that one determine at some point the internal diameter of the subject's uterine artery, whereupon, it becomes a simple matter to arrive at its cross-sectional area. This data together with a velocity measurement which tells how fast the blood is moving through the artery is all that is needed in the way of information in order to be able to calculate the uterine blood flow.

Several groups have attempted, however, to apply pulsed Doppler to the uterus. In 1983, Campbell et al (Lancet 1, 675-677) used this method to record the velocity patterns of the small arcuate arteries of the uterus in pregnant subjects. In March of 1985, Janbu et al (Acta Physiol Scand, 124:153-161, 1985) succeeded in recording blood flow velocity, but not its volume, in the uterine arteries of pregnant subjects using an ultrasound transducer placed on the abdomen. The main problem with this method was that a relatively low frequency three megahertz crystal had to be used to get adequate penetration of the signal and this combined with the attenuation of the signal by pelvic structures and the depth of sonication limited the resolution. As a consequence, this method only worked during pregnancy when the uterine arteries are enlarged to several times their non-pregnant diameter (4.5 mm vs. 1-2 mm). Also, there was no means of stabilizing the position of the transducer head on the abdomen for repeated measurements over a period of time. Even if this method could be improved to the degree where it became effective to measure blood flow in the non-pregnant state, there would still exist the problem of differentiating the uterine artery from a number of other arteries of similar size in the pelvis while, at the said time, eliminating measurements of flow velocities in close-lying uterine veins. Also, this method is currently limited to the approximate measurement of velocity spectra because accurate blood flow measurements would require the determination of vessel diameter and a reasonably accurate assessment of the angle of sonication, both of which would be extremely difficult to achieve externally.

In this same study, Janbu and his co-workers were able to also record blood flow patterns in the uterine arteries by using a small hand-held transducer which was inserted up into the lateral aspect of the upper vagina (vaginal fornix) just lateral to the cervix. This technique proved to be successful in eliminating some of the problems inherent in recording from the external surface of the abdomen and it produced good velocity spectra recordings. Resolution was improved through the use of a higher frequency crystal (6 megahertz) and positioning the crystal close to the uterine arteries where attenuation of the signals was minimal. On the other hand, this study was limited to the recording of velocity spectra since no provision was made for measuring the vessel diameter and, as a matter of fact, even the angle of sonication was only an estimate of the true angle. The major drawback of the method, however, was that the transducer had very poor positional stability and the signal was often disrupted by the slightest movement of the patient or the examiner.

Since medical ultrasound units are particularly susceptible to loss of signal or inaccuracy with relatively slight movements of the transducer, a number of rather complicated devices have been developed to minimize this problem. The prior art patents to Kunii et al U.S. Pat. No. 4,282,879 and Fraser U.S. Pat. No. 4,228,687 both reveal units designed to change the angle of incidence of the ultrasonic signal for imaging purposes while that of Atkov et al U.S. Pat. No. 4,483,344 discloses a platform supporting the transducer for movement from one position to another. These relatively large units are primarily designed for use on external surfaces of the body that are flat or only slightly rounded. Under no circumstances could these units be used in the vagina which is a narrow tubular structure with distensible walls into the apex of which projects a blunt, fibromuscular cervix of variable diameter with a variable angle of incidence.

Other stabilization methods employ fixed arrays of transducers to provide multisource illumination and detection of underlying structures. Meindl et al's U.S. Pat. No. 3,888,238 along with that of Plesset et al U.S. Pat. No. 4,409,982 both show fixed arrays of transducers used for imaging purposes; whereas, those of Soldner et al (U.S. Pat. No. 3,824,988); Ziedonis (U.S. Pat. No. 3,847,016); Specht et al (U.S. Pat. No. 4,241,611); and, Proudian (U.S. Pat. No. 4,398,539) all deal primarily with circular arrays for focusing purposes. It is highly unlikely that any of these units could be used for the purpose of measuring uterine blood flow from a situs within the subject's vagina alongside her cervix for the obvious reason that they are too large. The area just subadjacent to the uterine artery between the lateral aspect of the cervix and the lateral vaginal wall is only about 1-2 cm$^3$ in area. Moreover, these units are essentially "fixed" and depend upon multiple transducer arrays for the movable aspects of the apparatus such as they are. No provision is made or intended by means of which both the diameter of the uterine artery could be determined and then the array shifted to look along it at an angle of only a few degrees to the direction of blood flow through it.

Eden et al's U.S. Pat. No. 4,439,033 shows an intrauterine catheter into which fluid is introduced to expand it against the wall of the intrauterine cavity. Placement of an ultrasound transducer in such a unit poses several problems, not the least of which is the discomfort to the patient as the cervical canal is dilated and the risk of infection attendant to manipulation of the cervical canal. From the standpoint of the present invention, its use would induce reflex contractile activity in the uterus that would materially alter normal blood flow volumes. Such contractile activity is routinely seen with even minor manipulations within the cervical canal, e.g. dilation of the cervical canal, insertion of an intrauterine device, etc. Furthermore, it, like many of the other prior art devices, makes no provision for changing the incidence angle in order to measure both the vessel diameter and the velocity of the uterine blood flow.

The early U.S. Pat. No. 635,004 issued to Souder discloses a cervical cup having a central stem which is apparently inserted into the cavity of the cervix for the purpose of holding it in place. Once again, such a procedure involves a significant risk of infection, unwanted reflex contractile activity and its attendant alteration of normal uterine blood flow.

The relatively recent U.S. Pat. No. 4,355,643 issued to Laughlin et al discloses a carrier for a transducer that consists of a flexible concave dish to which a suction is applied to hold it in place against the subject's skin. Its shape renders it unsuitable for use within the tubular configuration of the vagina and, moreover, no provision is made for shifting the position of the transducer to take both the vessel diameter measurement and the low angle velocity reading along the uterine artery.

SUMMARY OF THE INVENTION

The internal diameter of the uterine artery along with the velocity of blood flow therethrough is determined in accordance with the teaching of the present invention by positioning the transducer alongside and in close proximity to the latter within the subject's vagina by supporting the crystal on the side of a rigid cervical cup which closely fits the cervix and is held in stable position thereon by the intrinsic suction generated by its placement, the cup thus forming a stable platform mounting the crystal. Since portions of the ultrasound signal are reflected back from any surface of different density, the ultrasound unit will receive reflections from both sides of the column of blood running in the uterine artery when oriented and manipulated such that it can sweep through an arc lying in a plane substantially at right angles to the direction of such blood flow. These tracings can then be used to measure the internal diameter of the uterine artery at which point it becomes a simple matter to calculate the cross-sectional area of an essentially cylindrical artery.

The only other information needed in order to calculate the flow is to determine the velocity of the blood flowing within the artery. This requires repositioning the transducer such that, instead of sweeping an arc lying in a plane perpendicular to the direction of blood flow, it faces upstream at a relatively small acute angle to the flow where its ultrasound beam will be reflected from the moving red blood cells. Since the frequency of the generated ultrasonic signal is known, by applying the well known principle of the Doppler Effect to determine the rise in the frequency resulting from the movement of these cells toward the transducer, it, once again, becomes very easy to determine the mean velocity with which the blood is moving through the uterine artery. The resulting mean velocity measurement together with the cross-sectional area of the uterine artery is all that is needed to determine the blood flow volume. The transducer can also be used to measure blood flow velocity away from the crystal: e.g. when the ultrasound beam is directed along the uterine artery as it progresses up the lateral side of the uterus.

One primary prerequisite in order to be able to accomplish the foregoing is, obviously, that of being able to accurately position the transducer in close proximity to the uterine artery and then manipulate it from a remote location outside the subject's body so as to be able to determine both the internal diameter of such artery along with the velocity of the blood flowing through it, all non-invasively and without traumatizing or otherwise disturbing the very organs one wishes to study. Once the foregoing objective has been reached, it can easily be done on both an instantaneous and a continuous basis, however, heretofore no one to applicants' knowledge has been able to do so.

A further refinement of the instant invention is that of a gating capability which is commonly used with pulsed Doppler and enables the operator to select the depth at which reflected signals will be detected by the ultrasound equipment, e.g. the unit can be set to only detect reflected signals at the specified depth and to ignore all other reflected signals. Such a feature greatly increases the accuracy of the readings because the measured reflections are limited to only those arising within the uterine artery. If the output of the ultrasound console is fed to a computer working in real time, blood flow volume can also be computed and displayed simultaneously.

Applicants have found that accurate measurements of uterine blood flow can, in fact, be determined non-invasively in humans by the simple, yet unobvious, expedient of mounting the transducer in a cradle movable about at least one axis, attaching the transducer thus cradled to the side of a close-fitting cervical cup to be mounted upon the subject's cervix in position such that the transducer can be moved in an arc lying in a plane substantially normal to the direction of blood flow therethrough for the purpose of determining the internal diameter of the vessel, and then by manipulating the transducer's cradle from a remote location outside the subject's body, repositioning the transducer such that it is directed upstream along the axis of blood flow at a small acute angle of, say, 5°–20° in order to determine the velocity of the blood flowing through the artery using the well known technique based upon the Doppler Effect phenomenon for processing the reflected signal or echo. If the cradle is designed such that it can only swing the transducer around a single axis, then it is necessary to turn the cup on the cervix such that the arc described by the transducer will lie in a plane essentially normal to the direction of arterial flow. On the other hand, if the cradle is designed for remote, but limited, substantially universal movement upon remote actuation, orientation of the cup on the cervix, while still important, is not nearly so critical.

It is, therefore, the principal object of the present invention to provide a novel and improved method for measuring uterine blood flow.

A second objective is to provide a unique device for carrying out the aforesaid method.

Another object of the invention herein disclosed and claimed is to accomplish the foregoing non-invasively.

Still another objective of the within-described invention is to make the desired measurement so as to not traumatize the subject and thus lead to an erratic response.

Further objects of the invention are to provide a uterine blood flow measurement apparatus and method of using said that are simple to use, versatile, accurate, reliable and safe.

Other objects will be in part apparent and in part pointed out specifically hereinafter in connection with the description of the drawings that follows.

BRIEF DESCRIPTION OF THE DRAWINGS

FIG. 4 is a still further enlarged fragmentary section showing the the transducer and its ball-type carrier and the cables that turn the carrier within its cradle both from side-to-side as well as up and down, portions of the latter having been broken away to conserve space;

FIG. 5 is a bottom plan view of the carrier of FIG. 4 illustrating the underside of the ball and the cables that control its movements;

FIG. 6 is a fragmentary top plan view to a smaller scale than FIGS. 4 and 5, showing the socket in the bottom of the housing in which the cradle rides;

FIG. 7 is a still further enlarged fragmentary perspective view much like FIG. 1 but showing a modified single axis system in which a cylindrical carrier replaces the ball of the preceding figures; and, FIG. 8 is a perspective view similar to FIG. 4 and to approximately the same scale, but showing the details of the cylindrical transducer carrier of FIG. 7.

DESCRIPTION OF THE PREFERRED EMBODIMENTS

Figure 1:
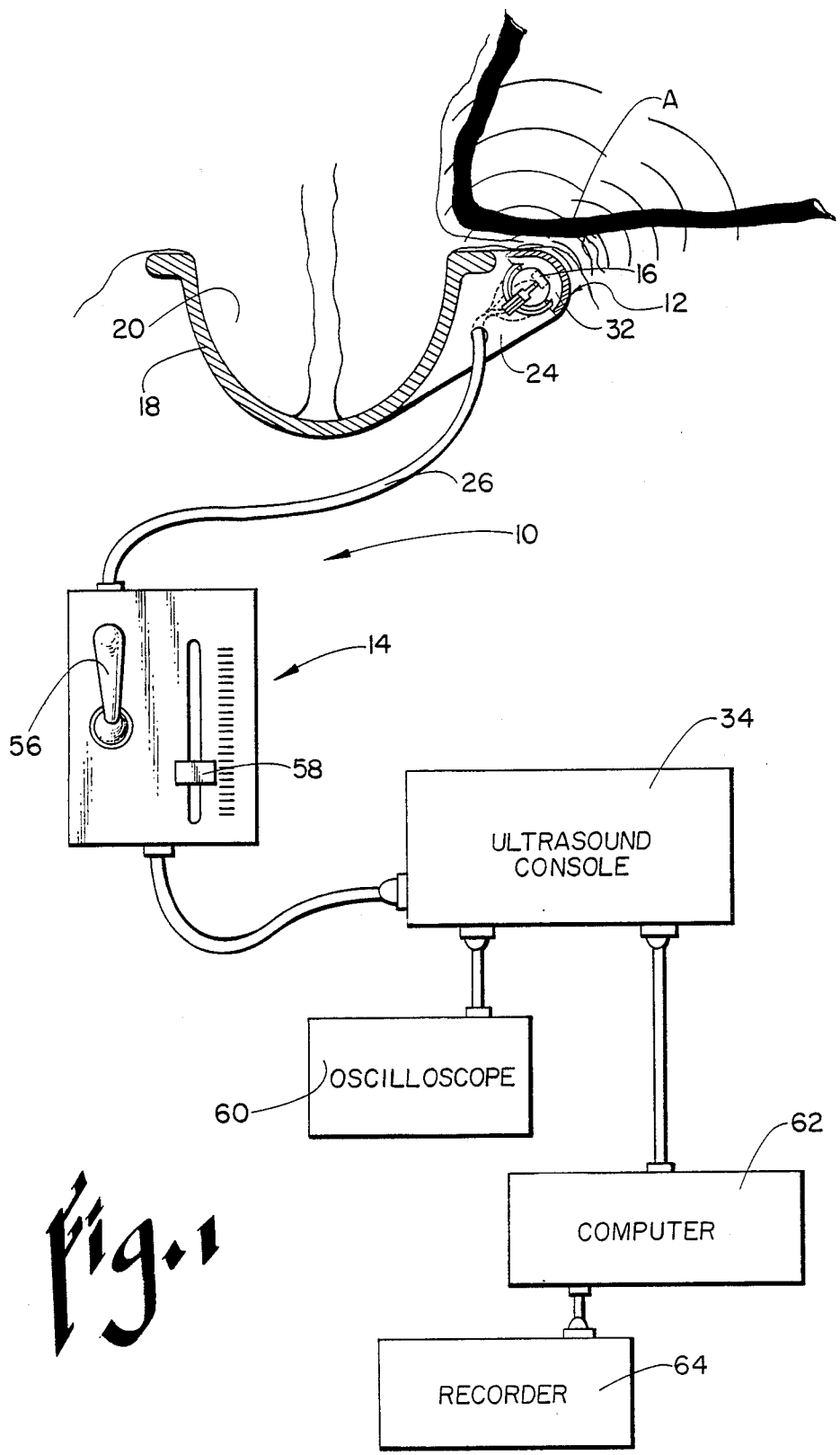
FIG. 1 is a schematic view to an enlarged scale showing the apparatus partly in section and partly in elevation positioned on the subject's cervix along with the remote actuating means and the related equipment required to translate the data coming from the transducer into a measurement of uterine blood flow.
Figure 2:
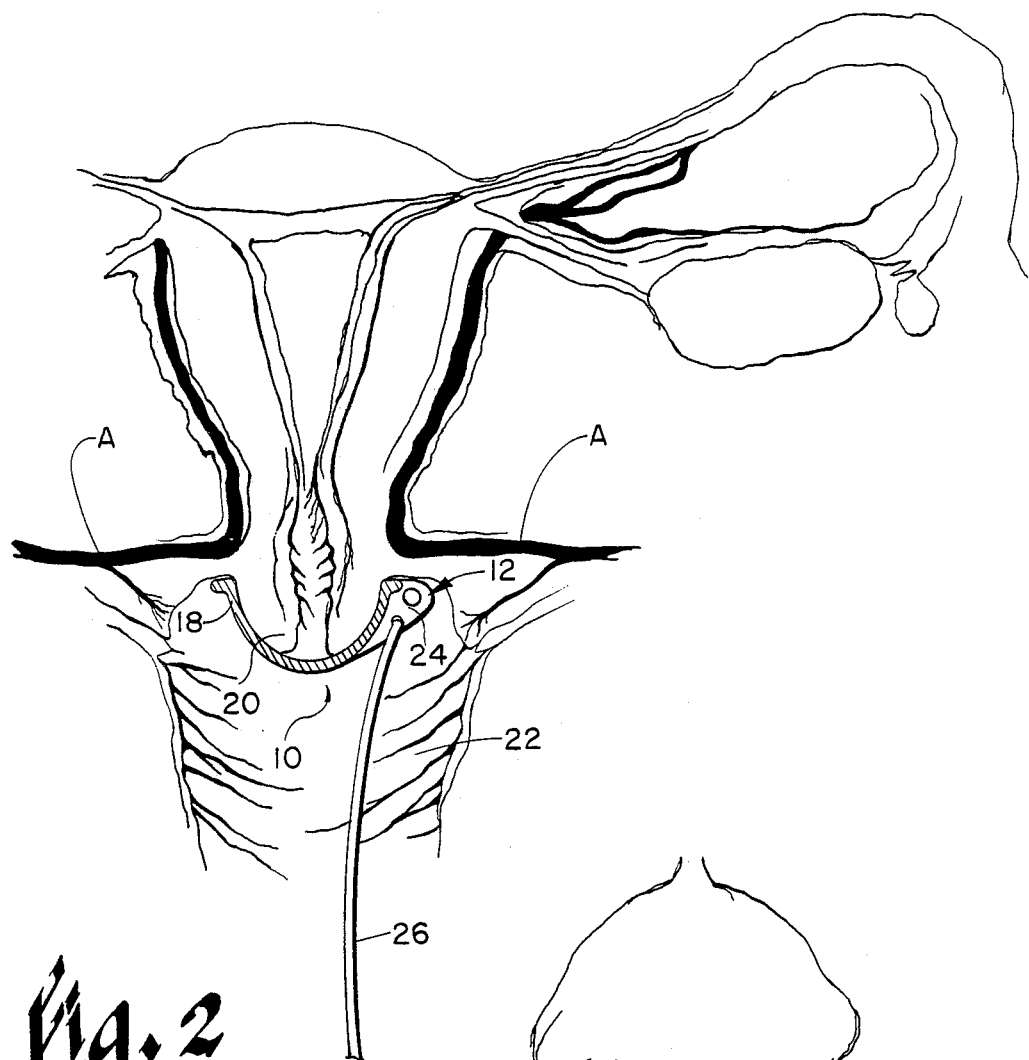
FIG. 2 is a fragmentary section taken generally on a perpendicular plane extending transversely of the human female's reproductive system showing the placement of the cup on the cervix of the subject so as to orient the transducer in its cradle proximate the uterine artery in position to measure its diameter in one position and the velocity of blood flow therethrough in a second position.

Referring next to the drawings for a detailed description of the present invention and, initially, to FIG. 1 for this purpose, reference numeral 10 has been chosen to identify the uterine blood flow measurement apparatus broadly while numerals 12 and 14 similarly designate the subassemblies that carry the transducer 16 and actuate the transducer carrier just mentioned. A modified cervical cup 18 sized to closely fit the subject's cervix 20 is placed thereon through the vagina 22 as shown in FIG. 2. This cup is modified to provide a hollow compartment or housing 24 alongside thereof which houses the transducer support subassembly 12 which will be described in considerably greater detail presently. Looking at FIGS. 1, 2 and 3, it will be seen that the uterine arteries A follow a path directly toward the cervix and then up along the lateral aspect of the uterus on both the right and left sides thereof and usually about the middle of the latter. As such, with the transducer carrier 12 positioned as shown in these three figures, the transducer 16 will ordinarily be in an ideal position i.e., directly under the artery, to be rotated about two mutually perpendicular axes necessary to develop the data needed for a blood flow determination.

Cup 18 is an important feature of the apparatus in that it provides a stable support for the transducer and the subassembly that moves the latter since it must remain in place for extended periods of time without moving if one is to obtain good data on changes which are phasic in nature as well as measurements of the changes taking place before, during and after active intervention. As a matter of fact, it can, if desired, be further modified to carry two transducers instead of just one i.e. one on each side of the cup, so that the blood flow in both arteries A can be measured simultaneously. This cup holds the carrier subassembly 12 in position just subadjacent the uterine artery even though the angle at which the cervix and uterus enter the vaginal canal varies because the cup mounts on the cervix. There are frequent and minor variations in position associated with physiologic changes in the abdomen that sometimes result in anterior and posterior displacement of the cervix and uterus. When properly fitted, these cups fit so tightly that from six to nine pounds of traction is required to dislodge them. They are also atraumatic to the cervix and can be inserted and removed by either the subject or the physician with minimal discomfort.

For present purposes it should be noted that the actuator subassembly 14 that controls the movements of the transducer carrier is located outside the subject's body but is connected thereto through the vagina by a small diameter sheath 26 that carries both the electrical supply wire from the transducer 16 to the ultrasound console along with two or more control cables 30 required to actuate the carrier, the latter having been shown most clearly in FIG. 4. All parts of the unit that are to be used internally must, of course, be made of materials approved for such use. In addition, the ultrasound crystal together with the platform or carrier supporting it for movement alongside the cervix must be small enough to fit between the latter and the lateral vaginal wall. The control cables are easily housed inside the common sheath with the electrical cable which carries only about 1.5 milliwatts of power. A power level of this order is adequate to drive a small ultrasound crystal some 3-6 mm in diameter at a power density of about 20 milliwatts/cm$^2$ which is well below what is considered a safe level for such use of 100 milliwatts/cm$^2$. Using a crystal having a resonate frequency of 5-7.5 megahertz insures that the investigator will be able to limit tissue penetration of the sound waves while providing good resolution of the reflected signal.

With particular reference to FIGS. 1 and 2, it can be seen that the housing 24 for the transducer carrier subassembly 12 lies lateral to at the lateral aspect of the cup and subadjacent to the uterine artery A, Preferably placing the transducer as close as practicable to the latter, say from 1-2 cm. This housing can be formed integral with the cup or, alternatively, be detachably connected thereto by a clip of some sort (not shown). Inside this housing is a cavity 32 (see FIGS. 1 and 6) which is filled with mineral oil or other ultrasound coupling medium and surrounds the carrier along with the transducer in a manner such that the sound waves will be transmitted without undue attenuation out to the artery A and back to the transducer.

In addition to providing a solid support for the transducer 16 as close as possible to the uterine artery, the key lies in being able to reposition the transducer so as to be able to take the two critical measurements necessary for determining uterine blood flow. Two alternative systems for taking these measurements have been illustrated. The first of these is the more complicated of the two while, at the same time, being the more versatile in that it provides for limited essentially universal movement of the transducer about mutually perpendicular axes; whereas, the alternative embodiment provides for limited angular movement about only one axis. The double-axis version 12 has been illustrated in FIGS. 1-6, inclusive, to which detailed reference will next be made.

Starting with FIGS. 4 and 5, it can be seen that a ball 36 with a pocket 38 sized and adapted to receive and hold the transducer 16 is cradled within a gimbal-like cradle that has been indicated in a general way by reference numeral 40. Lying in a plane paralleling the face of the transducer but located therebeneath so as to pass through the center of the sphere are a pair of mutually perpendicular axes of pivotal movement defined by pivot pairs 42 and 44. Pivots 42 are the shorter pair of the two and they are mounted in the smaller of two arcuate cradles 46 as seen in FIG. 4. The other longer pair of pivots 44, in turn, are received in the upstanding posts 48 of the larger cradle 50. Cradle 46 along with ball 36 is free to move within the confines of cradle 50 about the axis defined by pivot pair 44 thus enabling them to move from the full line position shown in FIG. 4 to their phantom-line position where the transducer 16 is tilted over to the right front. As seen in FIG. 6, the large cradle 50 is cradled within a suitably shaped arcuate track 32T in cavity 32 of compartment 24 for relative tiltable movement about an axis coincident with that defined by pivot pair 42 between the full and phantom-line positions it is shown occupying in FIG. 4 where the transducer is tilted to the left front. Similarly, the smaller cradle 46 rides in shallower track 32S. The combination of the two, of course, permits universal movement of the transducer within the limits of cradle movement.

FIGS. 4 and 5 both show the system of four sheathed cables which can be manipulated from a position externally of the subject's uterus to bring about remote actuation of the transducer. Wires 30a and 30a' control the movements of cradle 42 and thus tilt the ball 36 and associated transducer 16 about the axis defined by pivot pair 44. These cables are loosely housed and confined within grooves 52a and 52a' as shown most clearly in FIG. 5. They each enter the cradle from the opposite direction and are dead-ended at the remote end of their respective grooves as indicated at 54. The same is true with respect to cables 30b and 30b' within their grooves 52b and 52b' of the large cradle 50.

While pulling on one of these cables it is important that the force required to move the transducer carrier not dislodge the cervical cup and otherwise disturb the otherwise stable platform it provides for the latter and the transducer housed therein. On the other hand, these same cables must bend around relatively small radii within the shell or cradle supporting the carrier and, for this reason, they will not support any significant compression load. Nevertheless, this pull on one of the cables of a pair is, in fact, effectively resisted by the sheath housing it with the result that the cervical cup is not disturbed.

By pulling on cable 30a while simultaneously allowing movement of 30a' as above noted, the ball 36, transducer 16 and cradle 46 will all tilt together about the axis defined by pivot pair 44 and move from the full line position to the phantom-line position shown in FIG. 4. In like manner, pulling upon cable 30b' while permitting movement of cable 30b will cause the large cradle 50, ball 36 and the transducer 16 to pivot about the axis defined by pivot pair 42 thereby moving the transducer to the lower left phantom-line position of FIG. 4. A combination of these movements will, of course, move the transducer to intermediate positions between those shown in phantom-line in FIG. 4 as well as a near infinite variety of others where it is hidden from view as the ball is rotated away from the viewer. Note also, that as one cable of the operative pair is being pulled, the other is permitted to move as previously described. As a matter of fact, cables 30a and 30a' may be but opposite ends of the same cable actuated from some position intermediate its ends. The same may also be true, of course, of the companion cables 30b and 30b'.

The double-axis system of FIGS. 1-6 would be used in the following manner. First, in positioning the cervical cup on the subject's cervix, an attempt would be made to orient one of the two axes of pivotal movement so as to be directed along the portion of the uterine artery in which the blood flow is to be measured, i.e. on either the right side or the left side of the cervix with one of these axes extending transversely thereacross. Ordinarily, the uterine artery will be directly over the axis of pivotal movement thus oriented. With the sound waves propagated by the transducer directed upwardly at approximately right angles to the flow of blood through the uterine artery at its nearest point overhead, one should be able to get an accurate picture of the diameter of the artery from which it is a simple matter to calculate its cross section. Assume, for example, in FIG. 4 that the major axis of pivotal movement defined by pivot pair 44 is aligned substantially parallel to the direction of blood flow through the artery and that the transducer occupies the position in which it is shown in full lines; however, upon actuating cables 30a and 30a' back and forth it becomes obvious that the transducer in its full line position was not, in fact, directly underneath the artery but either all the way to one side or the other thereof or, perhaps, only looking at one edge, not its full thickness. It, therefore, becomes a simple matter to tilt the cradle 46 about axis 44 using cables 30a and 30a' until the reflected sound waves show the maximum diameter of the artery.

Having thus determined the diameter of the artery, the next step as previously noted is to use a pulsed signal to measure the velocity of flow through the artery. Wires 30b and 30b' would then be actuated to tilt the cradle 50 about the axis defined by pivot pair 42 thus orienting the axis of the transducer as close as possible to paralleling the flow through the artery. Since, obviously, the sound waves generated by the transducer cannot, as a practical matter, parallel the blood flow and still receive reflections because of being positioned underneath the artery some small distance and not inside thereof, it must, of necessity bear some angular relationship to the latter. It has been found that an acute angle less than 20° is quite satisfactory for such velocity measurements. Now, if, as will often be the case, the original orientation of the major axis defined by pivot pair 44, for example, was not quite accurate, there is no problem since cables 30a and 30a' can, once again, be used to bring the axis of the transducer in line with the middle of the artery while the other pair, 30b and 30b', are being actuated to place the transducer in position such that it looks along the artery at the smallest available acute angle. By being able to thus position the ball 36 in roughly an infinite number of available positions within the range of cradle movement, one can optimize the position of the transducer for both picturing the true diameter of the uterine artery and measuring the velocity of the blood flow through the latter, all non-invasively while performing each of the manipulations, except for placement of the apparatus on the cervix, from a remote location outside the subject's vagina.

Returning again briefly to FIG. 1, reference numeral 56 has been selected to designate the so-called "joy stick" which is one well known form of actuating mechanism that could be used to move all four cables 30a, 30a', 30b and 30b' simultaneously for purposes of orienting the transducer 16. No novelty is predicated upon such an actuating mechanism since such things are old in the art. Instead, it is intended as being merely illustrative and representative of one such actuator that could be used. External subassembly 14, in addition to housing the joy stick which is used for remote manipulation of the transducer carrier subassembly 12 also functions as a control center which may include such items as a preamplifier to amplify the voltage from the transducer and suitable electronics for indicating the angle of sonication, neither of which has been illustrated. Item 58 is intended to identify a slider mechanism operatively associated with the ultrasound console 34 by means of which the depth of gating can be controlled in a manner well known in the art and which, for this reason, forms no part of the present invention.

Likewise, ultrasound console 34 is of conventional design. Such a system generates a pulsed ultrasound signal while offering a choice of two different signal processing modes commonly known as the "A-mode" and "M-mode" either or both of which can be used to process the reflected signal or "echo" for the purpose of determining the diameter of the uterine artery in one position of the transducer. The reflections from this same pulsed signal can also be processed in the so-called Doppler-velocity mode in a second operative position of the transducer to measure the velocity of the blood flow through the uterine artery. Consoles of this type often include a digital display showing the depth of sonication while, at the same time, providing an audible rendition of the Doppler signal.

Item 60 is an oscilloscope that provides a visual display of either the A or M-mode signals depending upon how it is set. Both the A-mode and M-mode displays show the diameter of the artery directly on the scope. Item 62, on the other hand, is a computer into which is inputed the data from the ultrasound console 34 which information is processed to provide a visual display on its monitor showing the blood flow volume in real time. Finally, item 64 is a device like, for example, a chart recorder or printer of some type that will provide a permanent analog or digital record of the blood flow volume over time.

Figure 3:
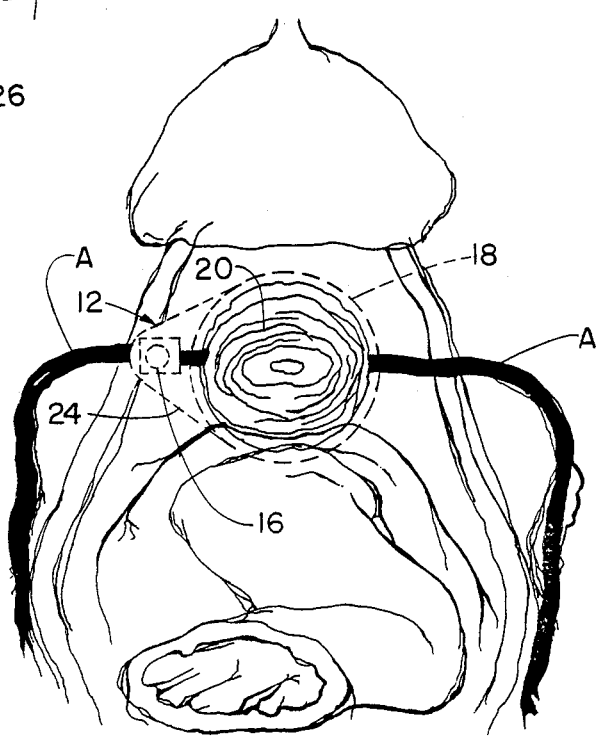
FIG. 3 is a fragmentary horizontal section taken at mid-pelvis to approximately the same scale as FIG. 2 but showing the cervix and the uterine arteries from above as they approach the midpoint of the latter from the side, the location of the transducer relative thereto just beneath the artery having been shown in phantom lines.

In FIG. 3 it can be seen that anatomically in the normal female reproductive system, the uterine arteries A approach the subject's cervix from both sides at essentially right angles thereto and about half way between the anterior and posterior surfaces thereof. If, as suspected, such a condition is present in most of the female subjects in which the uterine blood flow is to be measured, then the simpler single-axis carrier 12M may well suffice in place of the somewhat more complicated double-axis unit just described in that by merely properly orienting the cervical cup on the subject's cervix, the transducer 16 will automatically lie in proper position directly underneath the uterine artery as shown where the A-mode diameter measurement is to be made. If this is the situation, or nearly so, then there is little need for translating the transducer back and forth in a plane intersecting the uterine blood flow through the uterine artery at right angles thereto in order to be sure that the full diameter of the latter is measured. By using the single-axis carrier 12M and turning the cervical cup slightly one way or the other on the subject's cervix while monitoring the sonic reflections on the oscilloscope 60, the practitioner can be reasonably sure he or she is seeing the true diameter, of the artery, not some off-center chord of it.

FIGS. 7 and 8, to which reference will next be made, show the details of the single-axis carrier 12M. Housing 24M supported alongside the cervical cup 18 is slightly modified such that its carrier cavity 32M is appropriately shaped to accept a truncated more or less cylindrically-shaped cradle 66 for limited rotational movement about a single axis defined by pivot pair 68 at opposite ends thereof. Cavity 32M is further modified to eliminate the arcuate track 32T required for the large cradle 50 which is no longer needed. Instead, sockets 70 in the sides of the cavity 32M (FIG. 7) accept the pivot pins 68 for pivotal movement. Cavity 38 located in the truncated face of the cylinder is still used to house the transducer 16. The two sets of cable-receiving grooves of the previous two axis version are no longer needed and a single pair 72a and 72a' arranged in spaced parallel relation to one another encircle the cylindrical portion of the cradle 66. Sheathed actuating cables 74a and 74a' enter these grooves in opposite directions as before and are dead-ended in the remote ends thereof as indicated at 54. Axial bore 76 in one of the pivot pins receives the sheathed power cable 26/28 that supplies power to the transducer crystal 16.

A simplified cradle-actuating subassembly 14M is shown in FIG. 7 and it will be seen to include a base 78 atop which is mounted a lever 80 for pivotal movement about an axis intermediate its ends defined by pivot pin 82. The ends of actuating cables 74a and 74a' remote from the cradle are attached to posts 84a and 84a' located on top of the lever arm on opposite sides of the pivot pin 82. Movement of the lever arm from the phantom-line position into its full-line position, of course pulls on cable 74a while simultaneously permitting cable 74a' to move thereby rotating the cradle clockwise as viewed in FIGS. 7 and 8 all without exerting any force to pull the cervical cup off the subject's cervix.

With the transducer 16 in the phantom-line position of FIG. 7 and directly underneath the uterine artery as shown in this figure and FIG. 3, it will direct the ultrasonic signals across the artery A at approximately right angles to the flow of blood therethrough. With the ultrasound console set to display reflected sound waves in either the A-mode or the M-mode, it can provide the operator with reflections from the walls of the artery from which its internal diameter can be determined; provided, of course, that it is not displaced to one side thereof or the other. Should it be so displaced, a small angle of rotation of the cervical cup in the plane of FIG. 3 one way or the other will reveal the error and provide the proper reading of the arterial diameter.

Once this has been done, the cradle actuating subassembly 14M is manipulated as shown by moving the lever from its phantom-line position to its full-line one thereby shifting the cradle into its full-line position where the ultrasonic signals generated by the transducer crystal are directed along the artery at an acute angle thereto. With the ultrasound console 34 set to process the reflected ultrasound signal in the Doppler-velocity mode, the velocity of the blood flowing through the artery can be determined and this value together with the vessel's diameter enables one to easily calculate the flow.

Finally, it is significant to note that the apparatus and method forming the subject matter hereof are not concerned so much with "imaging" as was the case with the prior art ultrasonic systems used to visualize anatomical structures, but rather, the "positioning" of the transducer relative to the uterine artery. As the operator sweeps the transducer back-and-forth across the uterine artery, he or she can tell when the maximum reading is forthcoming and this, obviously, means that it is a true diametrical reading, not a chordal one. Also, there is a reasonable assurance at this point that the reading is taken at right angles to the flow by using the indexing mechanism forming a part of the apparatus that is tied to the movements of the transducer carrier and which provides an externally-visible indication of the direction in which the ultrasound signal is being generated. This can be validated by moving the transducer to-and-fro along the artery rather than back-and-forth across it and taking the minimum diametrical reading which reading, of course, should represent the one taken perpendicular to the artery.

Somewhat the same situation exists with respect to getting the velocity reading in the Doppler-mode. By sweeping the transducer up-and-down and from side-to-side until the maximum velocity reading is obtained tells the operator that the transducer is in the optimum position as nearly parallel to the direction of blood flow through the artery as it is possible to achieve from the position in which these reflections are being taken. The aforementioned indexing system which provides an external indication of the position of the transducer also, of course, lets the investigator know the approximate angle of sonication at which the velocity measurement is being taken.

By combining the gating capabilities of the ultrasound consoles so equipped, and knowing the angle of sonication, the method and apparatus can be even further refined to enable the operator to select an optimum angle for sonication to determine the velocity of the blood flow that is free of extraneous signals such as those coming from the uterine veins which lie in quite close proximity to the uterine arteries.

What is claimed is:

1. An ultrasonic apparatus for the non-invasive intravaginal measurement of uterine blood flow which comprises: a cervical cup shaped and sized to closely fit a cervix of a human female upon insertion into a vagina and to be tightly and stably held thereon in an atraumatic manner upon such insertion, means on said cup defining a housing alongside said cup to be located laterally of the cervix and positionable beneath one of the uterine arteries in close proximity thereto when said cup is in place on said cervix, cradle-forming means mounted within said housing means for limited angular movement relative to said housing means about at least a first axis of pivotal movement lying in a plane substantially perpendicular to the direction of blood flow within said uterine artery when said cup is in place on said cervix, transducer means for transmitting ultrasonic signals mounted upon said cradle-forming means for movement therewith between a first operative position in which the signals transmitted thereby intersect the blood flowing through the uterine artery thereabove at substantially right angles thereto and a second operative position in which said signals intersect said blood flow at an acute angle, and means for shifting the cradle-forming means between its first and second operative positions in a manner such that the position of said cervical cup on the cervix remains essentially undisturbed.

2. The apparatus set forth in claim 1 in which: the means for shifting the cradle-forming means comprises a first pair of short wire cables entering the cradle-forming means from opposite directions substantially at right angles to the first axis of pivotal movement, said short wire cables each having one end dead-ended on the cradle-forming means adjacent to the end thereof opposite the end in which they entered and the other ends thereof terminating near the point where said cables enter the vagina, said first pair of short wire cables being effective when one or the other thereof is pulled upon to rotate the cradle-forming means about its first pivotal axis.

3. The apparatus as set forth in claim 2 in which: the cradle-forming means includes a first cradle element carrying the transducer means and a second cradle element, said first cradle element being mounted in said second cradle element for limited pivotal movement about said first axis of pivotal movement, and said second cradle element being mounted within the housing means for limited pivotal movement about a second axis of pivotal movement intersecting said first axis of pivotal movement at right angles thereto, said first pair of short wire cables being operatively connected to the first cradle element, and means for sweeping the ultrasonic signals transmitted by said transducer means across the uterine artery thereabove about an axis generally paralleling the direction of blood flow through the uterine artery comprising a second pair of short wire cables entering the second cradle element from directions at substantially right angles to said second axis of pivotal movement, said second pair of short wire cables each having one end dead-ended on said second cradle element adjacent to the end thereof opposite the end at which they entered and the other ends thereof terminating near the point where said second pair of short wire cables enter the vagina, said second pair of short wire cables being effective when one or the other is pulled upon to rotate said second cradle element about said second axis of pivotal movement.

4. The apparatus as set forth in claim 3 in which: the first and second cradle elements are so interconnected to one another and to the housing means as to form a gimbal-type universal mounting for the transducer means.

5. The apparatus as set forth in claim 3 in which: the first cradle element comprises an arcuate yoke, and in which the second cradle element is spherically-shaped and cradled for pivotal movement within said yoke.

6. The apparatus a set forth in claim 1 in which: the cradle-forming means is substantially cylindrical and its axis is substantially coincident with said first axis.

7. The apparatus as set forth in claim 1 in which: the second position of the cradle-forming means is such that the velocity measurement signal intersects the uterine artery when said cervical cup is in place at an acute angle relative to the direction of blood flow through the uterine artery of less than 20°.

8. A method for measuring the volume of uterine blood flow which comprises the steps of: providing a cervical cup which is sized and shaped to closely fit a cervix of a human female upon insertion into her vagina and to be tightly held thereon in an atraumatic manner upon such insertion, non-invasively positioning said cervical cup onto the cervix in an atraumatic manner, providing a housing means on said cervical cup, locating the housing means on said cup to be spaced laterally of the cervix when said cervical cup is in position on said cervix, providing a trasnducer mean capable of transmitting ultrasonic signals within the vagina of a mammalian female, movably mounting said transducer means in said housing means laterally alongside the cervix beneath and in close proximity to a uterine artery, measuring the diameter of the uterine artery by directing a depth measurement signal thereacross at an angle substantially at right angles to the direction of blood flow therethrough, determining the cross sectional area of said uterine artery based upon said diametrical measurement, moving said transducer means relative to said cervical cup which is mounted in said housing so as to redirect the transducer means along the uterine artery at an acute angle opposing the direction of blood flow without substantially disturbing the position of said cervical cup on said cervix, determining the mean velocity of the blood flowing through the uterine artery, and determining the volume of blood flow based upon the aforesaid velocity measurement and cross-sectional area determination.

9. The method as set forth in claim 8 in which: the step of determining the mean velocity of blood flowing in the uterine artery includes directing ultrasonic signals toward the uterine artery at an angle of less than 20° to the direction of blood flow in that uterine artery.

10. The method as set forth in claim 8 in which the step of directing the ultrasonic signals includes transmitting such ultrasonic signals at a frequency of between approximately 5 and 7.5 megahertz.

11. The method as set forth in claim 8 in which the step of mounting said transducer means includes locating that transducer means between approximately 1 and 2 cm beneath the uterine artery.

12. The method as set forth in claim 8 further including rotating the transducer means in place alongside the cervix about an axis lying in a plane substantially perpendicular to the direction of blood flow through the uterine artery and taking the mean velocity measurement from a location outside the vagina.

13. The method as set forth in claim 12 further including rotating the transducer means in place alongside the cervix about an axis lying in a plane substantially paralleling the direction of blood flow through the uterine artery.

* * * * *